United States Patent
Isomoto

(10) Patent No.: US 7,424,822 B2
(45) Date of Patent: Sep. 16, 2008

(54) MICRO-HARDNESS MEASUREMENT METHOD AND MICRO-HARDNESS METER

(75) Inventor: Yoshinori Isomoto, Hiroshima (JP)

(73) Assignee: Renias Co. Ltd., Mihara-Shi, Hiroshima (JP)

( * ) Notice: Subject to any disclaimer, the term of this patent is extended or adjusted under 35 U.S.C. 154(b) by 0 days.

(21) Appl. No.: 11/640,913

(22) Filed: Dec. 19, 2006

(65) Prior Publication Data
US 2007/0157710 A1   Jul. 12, 2007

(30) Foreign Application Priority Data
Jan. 6, 2006   (JP) ............... 2006-001892

(51) Int. Cl.
*G01N 3/42* (2006.01)

(52) U.S. Cl. ............... 73/81; 73/82; 702/155; 702/166

(58) Field of Classification Search ............. 73/78, 73/79, 81, 82, 83, 85; 702/155, 166
See application file for complete search history.

(56) References Cited

U.S. PATENT DOCUMENTS

| | | | | |
|---|---|---|---|---|
| 4,848,141 A | * | 7/1989 | Oliver et al. | 73/81 |
| 5,999,887 A | * | 12/1999 | Giannakopoulos et al. | 702/33 |
| 6,134,954 A | * | 10/2000 | Suresh et al. | 73/81 |
| 6,155,104 A | * | 12/2000 | Suresh et al. | 73/81 |
| 6,247,355 B1 | * | 6/2001 | Suresh et al. | 73/82 |
| 6,718,820 B2 | * | 4/2004 | Kwon et al. | 73/81 |
| 6,778,916 B2 | * | 8/2004 | Lee | 702/42 |
| 6,851,300 B2 | * | 2/2005 | Kwon et al. | 73/85 |
| 6,883,367 B2 | * | 4/2005 | Feng et al. | 73/81 |
| 7,149,634 B2 | * | 12/2006 | Ma et al. | 702/41 |

FOREIGN PATENT DOCUMENTS

| | | |
|---|---|---|
| JP | H05-020691 | 1/1993 |
| JP | 2001-349815 | 12/2001 |
| JP | 3510411 | 9/2004 |

* cited by examiner

*Primary Examiner*—David A. Rogers
(74) *Attorney, Agent, or Firm*—Jean C. Edwards, Esq.; Akerman Senterfitt

(57) ABSTRACT

A micro-hardness measurement method for calculating the hardness of a test sample by pushing an indenter in the test sample and forming an indentation thereon, including: a loading step for extracting load data showing the relationship between load L applied to the indenter and a depth $\delta$ to which the indenter is pushed in from the surface of the test sample; an unloading step of extracting unloading data showing the relationship between the load L applied to the indenter after the load is unloaded and the depth $\delta$; a first step of judging, by comparing the unloading data with the load data, the load fluctuation amount from the maximum depth $\delta_0$ when unloading the load; and a second step of judging the load at the depth $\delta_1 (\delta_1 < \delta_0)$ when unloading the load or the load fluctuation amount in the vicinity of the depth $\delta_1$.

5 Claims, 4 Drawing Sheets

MICRO-HARDNESS MEASUREMENT METHOD AND MICRO-HARDNESS METER

CROSS-REFERENCE TO RELATED APPLICATIONS

This application claims priority from Japanese Patent Appln. No. 2006-001892, filed Jan. 6, 2006, the contents of which are herein incorporated by reference in their entirety.

BACKGROUND OF THE INVENTION

1. Field of the Invention

The present invention relates to a micro-hardness measurement method for measuring the hardness of a test sample by forming an indentation or impression by pushing an indenter into a test sample, and a micro-hardness meter therefor, and in particular, to a micro-hardness measurement method and a micro-hardness meter, which are best suitable for calculating the hardness of a test sample in which a hard surface layer is formed on the surface of a soft substrate.

2. Description of the Prior Art

Conventionally, as a measurement method of the hardness, a diagonal length measurement system by which the hardness is obtained based on the length of a diagonal line of an indentation formed by an indenter, such as Vickers hardness, and a depression depth measurement system by which the hardness is obtained based on the depth of a depression, exist. In the diagonal length measurement system, the hardness is obtained by using a calculation expression of Hardness= (Maximum load)/(Surface area of permanent depression) from the surface area of a permanent depression calculated based on the diagonal length of an indentation. Also, in the depression depth measurement system, the hardness is obtained by calculating the surface area of a depression based on a push-in depth of an indenter when an indentation is formed and by using the above-described calculation expression.

Here, in order to measure the diagonal length of an indentation by a microscope in the diagonal length measurement system, it is necessary to form an indentation whose diagonal length is at least 10 micrometers or so. However, where the hardness of a test sample in which a hard film is formed on the surface of a substrate, there was a problem that the hardness of only the film cannot be obtained since influences on the hardness of the substrate are exerted or an indenter penetrates the film. In addition, since the depression depth of the indentation is made equivalent to the thickness of the film and the indentation is influenced by the substrate, there was another problem that it is difficult to read the diagonal length of the indentation by using an optical type microscope.

On the other hand, since, in the depression depth measurement system, the depression depth of an indentation is measured based on the push-in amount of an indenter, it is possible to measure the hardness of an object even if the object is a micro indentation for which the diagonal length cannot optically be measured.

However, since, in the depression depth measurement system, a test sample is deflected if an indenter is forcedly pushed therein where the elastic deformation ratio of the test sample is great when forming an indentation, the push-in depth of the indenter is made greater than the depth of the indentation (permanent depression), wherein the surface area of a depression calculated from the push-in depth of the indenter becomes greater than the surface area of the indentation (permanent depression) after the load is unloaded, and there is still another problem that the hardness calculated by the (maximum load)/(surface area of permanent depression) is underestimated.

Hereinafter, a description is given of the problem with reference to the drawings.

FIG. 6 is a schematic diagram depicting a state where an indenter is pushed in a test sample in which a hard surface layer is formed on the surface of a soft substrate.

In the drawing, reference numeral 100 denotes a test sample, 101 denotes a soft substrate such as a synthetic resin, etc., 102 denotes a hard surface layer such as glass, which is formed on the surface of the substrate 101. Reference numeral 103 denotes an indenter formed to be like a pyramid.

When the indenter 103 is pushed in the surface layer 102 of the test sample 100 with a load given to the indenter 103, the substrate 101 and the surface layer 102 are elastically deformed as depicted in FIG. 6(b). If the indenter 103 is further pushed in, the distortion is increased, wherein the elastic deformation of the substrate 101 and the surface layer 102 is also increased, and at the same time, plastic deformation occurs (FIG. 6(c)). When the load given to the indenter 103 is released and is unloaded, if the indenter 103 has not reached the substrate 101, the deflection of the surface layer 102 and the elastic deformation of the substrate 101 are eliminated, wherein the plastic deformation appears on the surface of the test sample 100 as a permanent depression (FIG. 6(d)).

Therefore, the push-in depth of the indenter 103 becomes deeper than the depth of an indentation (permanent depression) after the load is unloaded, and the surface area of the depression calculated from the push-in depth of the indenter 103 becomes wider than the surface area of the indentation (permanent depression) after the load is unloaded, wherein the hardness calculated by the (maximum load)/(surface area of the permanent depression) is underestimated.

As prior art to solve the problem, for example, Japanese Patent No. 3510411 discloses a micro-hardness measurement method including the steps of: measuring depths of a plurality of indentations or impressions formed by different loads, respectively; calculating respective depth correction values in which respective depth measurement values are corrected in response to the profiles of the tip ends of the indenters; measuring respective lengths of diagonal lines of the plurality of indentations or impressions; inversely calculating the depths of the indentations based on the hardness calculated on the basis of the respective measurement values of the diagonal lines; correcting the actually measured values of the depths of the indentations by means of a correction equation defined on the basis of the correction values of depth and the inversely calculated values of the depth; and calculating the hardness based on the after-correction depth and the load for forming indentations.

Japanese Published Examined Patent Application No. Hei-5-20691 discloses an ultra-micro-hardness meter including means for calculating a proportional constant K and a dynamic hardness of a test sample by the least squares method based on a predetermined calculation equation from a load P given to an indenter at an optional measurement point, a displacement d of the indenter at the load, and a constant cc determined by the profile of the indenter.

Japanese Published Unexamined Patent Application No. 2001-349815 discloses a method for determining the hardness of a thin film, including the steps of: obtaining the ratio of hardness to elastic modulus of the thin film of a measurement object based on an approximate expression in which the relationship between work done by an indenter when the indenter is loaded for being pushed in a thin film of the measurement object, work done by the thin film onto the indenter when being unloaded, and ratio of hardness to elastic modulus of various materials are linearly approximated; next obtaining the contact area of the indenter at the maximum load; and acquiring the hardness of the thin film.

However, the following problems in the prior art described above exist.

In the art disclosed by Japanese Patent No. 3510411, since the correction equations differ from each other depending on the profile and material of the indenter, the depth of an indentation and the length of the diagonal line are measured whenever the profile and material of the indenter change, wherein it is necessary to calculate the correction value and carry out correction. Therefore, there is a problem that the operation is very cumbersome.

In the art disclosed by Japanese Published Examined Patent Application No. He-5-20691, an error occurs when calculating the proportional constant K and the dynamic hardness of a test sample by means of the least squares method, and there is another problem that the measurement accuracy is lowered. Additionally, since the hardness is calculated with the profile of the indenter taken into consideration based on the relationship between the load P and displacement d at an optional measurement point, no consideration is paid to the push-in depth of the indenter, wherein there is a premise that the hardness is constant in the depth direction of the test sample. Therefore, where the hardness is calculated in regard to a test sample the hardness of which changes in the depth direction as in a test sample in which a hard surface layer is formed on the surface of a soft substrate, there is still another problem that the error becomes remarkably large, depending on the push-in depth of the indenter.

In the art disclosed by Japanese Published Unexamined Patent Application No. 2001-349815, since an error occurs when the relationship of the ratio of hardness to elastic modulus of various materials is linearly approximated, and the error is accumulated when calculating the hardness, there is still another problem that the measurement accuracy is lowered. Also, since the hardness H is obtained by a calculation equation of $H = P_{max}/A$ from the maximum load $P_{max}$ and the contact area A of an indenter at the maximum load, the art is a hardness measurement method aiming at metal materials the test sample of which is unlikely to be deflected and elastically deformed, and there is a problem that the method is short of applications.

SUMMARY OF THE INVENTION

The present invention is to solve the above-described problems. It is therefore an object of the invention to provide an excellent micro-hardness measurement method, which does not require any cumbersome operations to carry out correction by measuring the depth of an indentation and the length of a diagonal line thereof a plurality of times and calculating a correction value, is excellent in operability as hardness can be calculated with simple operations, and is capable of calculating the hardness at high accuracy without being influenced by the profile of an indenter, wherein an error is unlikely to occur, and which is further capable of calculating the hardness of a test sample having such a hard surface layer, on which only a micro load is permitted to be loaded, and only a micro indentation whose diagonal line length is 10 micro meters or less is permitted to be formed, therefore being excellent in applicability.

Also, it is another object of the invention to provide a micro-hardness meter having excellent operability, which is capable of automatically calculating the hardness in a short time, calculating the same at high accuracy without being influenced by the profile of an indenter, wherein an error is unlikely to occur, and further calculating the hardness of a test sample having such a hard surface layer, on which only a micro load is permitted to be loaded, and only a micro indentation whose diagonal line length is 10 micrometers or less is permitted to be formed, therefore being excellent in applicability.

In order to achieve the above-described objects, a micro-hardness measurement method and a micro-hardness meter according to the present invention are constructed as described below.

A micro-hardness measurement method according to the present invention is a micro-hardness measurement method for calculating the hardness by pushing an indenter in a test sample and forming an indentation, including: a loading step for extracting load data showing the relationship between load L applied to the indenter and a depth $\delta$, to which the indenter is pushed in from the surface of the test sample, to the maximum load $L_0$ (load at the maximum depth $\delta_0$); an unloading step of extracting unloading data showing the relationship between the load L applied to the indenter after the load is unloaded and the depth $\delta$; a first step of judging, by comparing the unloading data with the load data, whether or not the load fluctuation amount from the maximum depth $\delta_0$ when unloading the load is within the first permissible range; a second step of judging, when it is judged that the load fluctuation amount is within the first permissible range, whether or not the load at the depth $\delta_1$ ($\delta_1 < \delta_0$) when unloading the load or the load fluctuation amount in the vicinity of the depth $\delta_1$ is within the second permissible range; a step of calculating a virtual depth $\delta_v$ based on the inclination of a tangent line at the maximum depth $\delta_0$ of the unloading curve obtained from the unloading data (a) when it is judged that the load fluctuation amount is not within the first permissible range or regarding the maximum depth $\delta_0$ as a virtual depth $\delta_v$, or of calculating a virtual depth $\delta_v$ based on the inclination of a tangent line at the depth $\delta_1$ of a load curve obtained from the load data (b) when it is judged that the load or the load fluctuation amount is not within the second permissible range; and a step of calculating the hardness based on the virtual depth $\delta_v$ and the maximum load $L_0$.

With such a construction, the following action can be brought about.

Since, in a test sample such as metals in which deflection due to elastic deformation is unlikely to occur, the test sample is hardly restored from the maximum depth $\delta_0$ after the load is unloaded, the unloading data are greatly deviated from the load data in the vicinity of the maximum depth $\delta_0$. In the first judging step, it is judged whether or not the load fluctuation amount from the maximum depth $\delta_0$ is within a set first permissible range, and it is judged whether or not the unloading data are deviated from the load data. When it is judged not to be within the first permissible range, that is, when it is judged that the unloading data are deviated from the load data, the inclination of a tangent line at the maximum depth $\delta_0$ of the unloading curve obtained from the unloading data is obtained in the virtual depth calculating step, and the depth at the load L=0 (where the load is completely unloaded) is calculated based on the inclination. In addition, when it is judged in the first judging step that the unloading data are greatly deviated from the load data, the maximum depth $\delta_0$ is regarded as the virtual depth $\delta_v$. Next, the calculated depth or the maximum depth is regarded as a depth (virtual depth $\delta_v$) by which the surface area of an indentation (permanent depression) can be calculated, and in the hardness calculating step, the hardness may be calculated based on the virtual depth $\delta_v$ and the maximum load $L_0$.

Where an indenter is pushed in a test sample, in which deflection due to elastic deformation is likely to occur, such as a test sample in which a hard surface layer is formed on the surface of a soft substrate until reaching the maximum load $L_0$ (a set test force), and next the load is unloaded, the load L that is the same intensity as when being loaded is loaded from the test sample onto the indenter due to elastic restoration of the test sample at the beginning of unloading where the indenter does not completely break down the surface layer of the test sample. Therefore, the unloading data at the beginning of unloading is almost coincident with the load data based on Hooke's law. Since the restoration force decreases due to plastic deformation of the test sample as the deflection of the test sample decreases in line with advancement of unloading, the load L applied from the test sample to the indenter becomes smaller than the load L applied by the indenter onto the test sample when loading, wherein the unloading load is deviated from the load data. In the second judging step, the unloading data are compared with the load data, and it is investigated from which depth $\delta_1$ ($0<\delta_1<\delta_0$) deviation of the unloading data from the load data began. When it is judged that the load at the depth $\delta_1$ or the load fluctuation amount in the vicinity of the depth $\delta_1$ is not within the second permissible range, that is, when it is judged that deviation of the unloading data from the load data begins from the depth $\delta_1$, it means that the plastic deformation of the test sample is made dominative from the depth $\delta_1$. Herein, if, in the virtual depth calculating step, a tangent line of the load curve obtained from the load data is obtained, and the depth is calculated (a tangent line is extrapolated until the load becomes 0) when the load of a tangent line is L=0 (when the load is completely unloaded), the depth can be regarded as the depth (virtual depth $\delta_v$) by which the surface area of the indentation (permanent depression) can be calculated. Next, in the hardness calculating step, it is possible to calculate the hardness based on the virtual depth $\delta_v$ and the maximum load $L_0$.

Since the micro-hardness measurement method according to the invention is provided with the first judging step, the second judging step and the virtual depth calculating step, it is possible to calculate the hardness in both a test sample such as metals, in which deflection is unlikely to occur, and a test sample, in which deflection is likely to occur, like a test sample in which a hard surface layer is formed on the surface of a substrate. The method is excellent in versatility.

Since load data by which load is given to an indenter to push the indenter in a test sample and unloading data when unloading from the indenter may be extracted, and the virtual depth $\delta_v$ may be calculated based on the data, the method does not require any cumbersome operation by which a correction value is calculated by measuring the depth of an indentation and the length of the diagonal line thereof a plurality of times and carrying out correction. Therefore, the method is able to calculate the hardness with simple operations and is excellent in operability.

Since the load curve is comparatively simple, it is possible to almost accurately obtain the inclination of a tangent line at the depth $\delta_1$ of the load curve in the virtual depth calculating step after the second judging step, wherein an error is unlikely to occur, and the method is not influenced by the profile of the indenter. Therefore, it is possible to calculate the hardness at high accuracy.

Since the unloading curve is comparatively simple where it is judged in the first judging step that the load fluctuation amount is not within the first permissible range, it is possible, in the virtual depth calculating step after the first judging step, to almost accurately obtain the inclination of a tangent line at the maximum depth $\delta_0$ of the unloading curve, wherein an error is unlikely to occur, and the method is not influenced by the profile of the indenter. Therefore, it is possible to calculate the hardness at high accuracy.

Since it is not necessary to measure the actual depth of the indentation and the actual length of the diagonal line of the indentation, it is possible to calculate the hardness of a test sample having such a hard surface layer, on which only a micro load is permitted to be loaded, and only a micro indentation whose diagonal line length is 10 micrometers or less is permitted to be formed. Therefore, the method is excellent in applicability.

Herein, the loading step is to extract the load data (depth-load data) showing the relationship between the load L loaded to an indenter to the maximum load $L_0$ and the depth $\delta$ (including the deflection of a test sample) to which the indenter is pushed in from the surface of the test sample. Thus, it is possible to directly extract data showing the relationship between the depth $\delta$ and the load L. Also, data showing the relationship between the time T, during which the load is applied to the indenter, and the depth $\delta$ are extracted. Separately therefrom, data showing the relationship between the time T, during which the load is applied to the indenter, and the load L are extracted, wherein two types of these data are synthesized, and it is possible to extract load data showing the relationship between the load L and the depth $\delta$.

The unloading step extracts unloading data (depth-load data) showing the relationship between the load L which the test sample applies to the indenter based on its elastic force and the depth $\delta$ (including the deflection of the test sample) at which the indenter is pushed in from the surface of the test sample. Thus, it is possible to directly extract data showing the relationship between the depth $\delta$ and the load L. In addition, data showing the relationship between the elapsed time T after the load is unloaded and the depth $\delta$ and further, separately therefrom, data showing the relationship between the elapsed time T after the load is unloaded and the load L are extracted, wherein two types of these data are synthesized, and it is possible to extract the unloading data showing the relationship between the load L and the depth $\delta$.

The first permissible range is a permissible range for judging whether or not the unloading data are deviated from the load data from the maximum depth $\delta_0$, and the range may be determined by using, as an index, the ratio of the load fluctuation amount in a micro range from the maximum depth $\delta_0$ of the unloading data to the load fluctuation amount in a micro range to the maximum depth $\delta_0$ of the load data. Also, the range may be determined by using, as an index, the ratio of the load at a depth slightly shallower than the maximum depth $\delta_0$ of the unloading data to the load at the same depth as the vicinity of the maximum depth $\delta_0$ of the load data.

The load fluctuation amount when being loaded to the maximum depth $\delta_0$ may be obtained by a difference calculus based on the load data in a micro range in the vicinity of the maximum depth $\delta_0$. Or, it may be expressed by the inclination of a tangent line at the maximum depth $\delta_0$ that is obtained by differentiating the load curve (depth-load curve). Although the first permissible range may be established in an almost constant range, not depending on the material of a test sample, it may also be appropriately established in accordance with the velocity, etc., of the indenter when unloading.

In the first judging step, it is judged whether or not the load fluctuation amount when unloading from the maximum depth $\delta_0$ is within the first permissible range. The load fluctuation amount when unloading from the maximum depth $\delta_0$ may be expressed by the inclination of a tangent line at the maximum depth $\delta_0$ of the unloading curve (depth-load curve) that is obtained from the unloading data. The inclination may be obtained by differentiating the unloading curve. In addition, it may be obtained from the unloading data by a difference calculus.

Also, in the first judging step, it is possible to judge, using a statistical method, whether or not the unloading data is deviated from the first permissible range. This is because consideration is paid to variation in data.

The second permissible range is a permissible range for judging at which depth $\delta_1$ ($0<\delta_1<\delta_0$) the unloading data began to be deviated from the load data, wherein the range may be determined by using, as an index, the ratio of the load at the depth $\delta_1$ of the unloading data to the load at the depth $\delta_1$ of the load data. In addition, the range may be determined by using, as an index, the ratio of the load fluctuation amount in the vicinity of the depth $\delta_1$ of the unloading data to the load fluctuation amount in the vicinity of the depth $\delta_1$ of the load data. The load fluctuation amount when loading in the vicinity of the depth $\delta_1$ may be obtained from the load data in the vicinity of the depth $\delta_1$ by a difference calculus, or may be expressed by the inclination of a tangent line at the depth $\delta_1$ obtained by differentiating the load curve (depth–load curve). Although the second permissible range may be established in an almost constant range, not depending on the material of a test sample, it may also be appropriately established in accordance with the velocity, etc., of an indenter when unloading.

In the second judging step, it is judged whether or not the load or the load fluctuation amount when unloading at the depth $\delta_1$ is within the second permissible range. The load fluctuation amount when unloading in the vicinity of the depth $\delta_1$ may be expressed by the inclination of a tangent line at the depth $\delta_1$ of the unloading curve (depth–load curve) obtained by the unloading data. The inclination may be obtained by differentiating the unloading curve. In addition, it may be obtained from the unloading data by a difference calculus.

In the virtual depth calculating step, the inclination of a tangent line of the unloading curve at the maximum depth $\delta_0$ may be obtained by a differential value of an approximate expression after acquiring the approximate expression of the unloading data. In addition, the inclination may be obtained from a difference value of the vicinity of the maximum depth $\delta_0$ of the unloading data without acquiring the approximate expression. Further, the inclination of a tangent line of the load curve at the depth $\delta_1$ may be obtained by a differential value of an approximate expression after acquiring the approximate expression of the load data. Still further, the inclination may also be obtained by a difference value of the vicinity of the depth $\delta_1$ of the load data without acquiring the approximate expression.

Herein, the virtual depth $\delta_\nu$ may be obtained as described below.

Where it is judged in the first judging step that the load fluctuation amount is not within the first permissible range, when the unloading data are greatly deviated from the load data and from the maximum depth $\delta_0$ (when the inclination of a tangent line at the maximum depth $\delta_0$ of the unloading curve is greatly different from the inclination of a tangent line at the maximum depth $\delta_0$ of the load curve), the maximum depth $\delta_0$ may be regarded as a virtual depth $\delta_\nu$. Plastic deformation is dominative in an indentation. Also, the maximum depth $\delta_0$ being regarded as the virtual depth $\delta_\nu$ may be corrected by an interpolation method in accordance with the degree of deviation between the unloading data and the load data. This is because the error is decreased.

Where it is judged in the second judging step that the load or the load fluctuation amount is not within the second permissible range, $m_1=df(\delta)/d\delta$ is established where it is assumed that the load curve is $L=f(\delta)$, and the inclination of the load curve at a depth $\delta_1$ is $m_1$ when the load is $L_1$, and the equation of a tangent line of the load curve can be expressed as follows:

$$L-L_1=m_1(\delta-\delta_1) \quad (1)$$

where the load is $L_1$ and the depth is $\delta_1$.

Since $\delta$ when completely unloaded (load L=0) is regarded as a virtual depth $\delta_\nu$, expression (2) is established by substituting the virtual depth $\delta_\nu$ in the expression (1)

$$-L_1=m_1(\delta_\nu-\delta_1) \quad (2)$$

Based on the expression (2), $$\delta_\nu=\delta_1-L_1/m_1 \quad (3)$$

Therefore, the virtual depth $\delta_\nu$ is made into $\delta_1-L_1/m_1$.

By taking the profile of an indenter into consideration in respect to the virtual depth $\delta_\nu$ (depth of permanent depression) obtained in the virtual depth calculating step, the surface area of the permanent depression of an indentation can be obtained. Therefore, in the hardness calculating step, it is possible to calculate the hardness by calculating (Maximum load $L_0$)/(Surface area of permanent depression).

The present invention is featured, in addition to a micro-hardness measurement method discussed above, in being constructed so that the upper limit of the first permissible range is defined by a conversion value $n_0/m_0$ of the ratio of the inclination $n_0$ of a tangent line at the maximum depth $\delta_0$ of the unloading curve to the inclination $m_0$ of a tangent line at the maximum depth $\delta_0$ of the load curve.

With the construction, the following actions can be brought about in addition to the actions discussed above.

Since the conversion value $n_0/m_0$ of the ratio of the inclinations $n_0$ and $m_0$ of tangent lines is obtained in the first judging step and it is judged whether or not the value exceeds the upper limit of the first permissible range, it is possible to simplify the setting of the first permissible range, and its detection sensitivity can be increased.

The present invention is featured, in addition to a micro-hardness measurement method discussed above, in being constructed so that the upper limit of the second permissible range is defined by a conversion value $n_1/m_1$ of the ratio of the inclination $n_1$ of a tangent line at the depth $\delta_1$ ($\delta_1<\delta_0$) of the unloading curve to the inclination $m_1$ of a tangent line at the depth $\delta_1$ of the load curve.

With the construction, the following actions can be brought about in addition to the actions discussed above.

Since the conversion value $n_1/m_1$ of the ratio of the inclinations $n_1$ and $m_1$ of tangent lines is obtained in the second judging step, and it is judged whether or not the value exceeds the upper limit of the second permissible range, it is possible to simplify the setting of the second permissible range, and its detection sensitivity can be increased.

The present invention is a micro-hardness meter including: (a) a load device for forming an indentation on a test sample by applying a load to an indenter: (b) a load sensor for detecting a load L at which the indenter applies to the test sample when loading, and a load L at which the test sample applies to the indenter when unloading; (c) a displacement meter for detecting a depth $\delta$ to which the indenter is pushed in from the surface of the test sample; (d) memory means for storing, based on information from the load sensor and the displacement meter, load data showing the relationship between the load L and the depth δ when loading, unloading data showing the relationship between the load L and the depth δ when unloading, and the maximum depth $δ_0$ and maximum load $L_0$ (load at the maximum depth $δ_0$); and (e) calculating means for comparing the unloading data with the load data and judging whether or not the load at the depth $δ_1$ ($δ_1<δ_0$) when unloading or the load fluctuation amount in the vicinity of the depth $δ_1$ is within the second permissible range, calculating the virtual depth $δ_v$ based on the inclination of a tangent line at the depth $δ_1$ of the load curve, which is obtained from the load data, when it is judged that the load or the load fluctuation amount is not within the second permissible range, and calculating the hardness based on the virtual depth $δ_v$ and the maximum load $L_0$.

With the construction, the following actions can be brought about.

Where an indenter is pushed in a test sample, in which deflection due to elastic deformation is likely to occur, such as a test sample in which a hard surface layer is formed on the surface of a soft substrate until reaching the maximum load $L_0$ (a set test force), and next the load is unloaded, the load L that is the same intensity as when being loaded is loaded from the test sample onto the indenter due to elastic restoration of the test sample at the beginning of unloading where the indenter does not completely break down the surface layer of the test sample. Therefore, the unloading data at the beginning of unloading is almost coincident with the load data based on Hooke's law. Since the restoration force decreases due to plastic deformation of the test sample as the deflection of the test sample decreases in line with advancement of unloading, the load L applied from the test sample to the indenter becomes smaller than the load L applied by the indenter onto the test sample when loading, wherein the unloading load is deviated from the load data. Utilizing the characteristics, the load data are stored in the memory means and are compared with the unloading data by using the calculating means, and it is investigated from which depth $δ_1$ ($0<δ_1<δ_0$) deviation of the unloading data from the load data began. Where it is judged that the load at the depth $δ_1$ or the load fluctuation amount in the vicinity of the depth $δ_1$ is not within the second permissible range, that is, when it is judged that the unloading data begins to be deviated from the load data from the point of depth $δ_1$, a tangent line of the load curve obtained by the load data is obtained, and a depth at the load L=0 (when completely unloaded) of the tangent line is calculated, and the depth is regarded as the depth (virtual depth $δ_v$) by which the surface area of the indentation (permanent depression) can be calculated, wherein it is possible to calculate the hardness based on the virtual depth $δ_v$ and the maximum load $L_0$.

Since the load data by which load is given to the indenter to push the indenter in the test sample and the unloading data when unloading the indenter are extracted, and the virtual depth $δ_v$ is calculated based on these data, no cumbersome operation is required, which carries out correction by measuring the depth of the indentation and the length of the diagonal line thereof a plurality of times and calculating the correction value. Therefore, the hardness can be calculated with simple operations and the operability thereof is excellent.

Since the load curve is comparatively simple, the calculating means can almost accurately obtain the inclination of a tangent line at depth $δ_1$ of the load curve, wherein an error is unlikely to occur, and the hardness can be calculated at high accuracy without being influenced by the profile of the indenter.

Since it is not necessary to measure the actual depth of an indentation and actual length of the diagonal line of the indentation, it is possible to calculate the hardness of a test sample having such a hard surface layer, on which only a micro load is permitted to be loaded, and only a micro indentation whose diagonal line length is 10 micrometers or less is permitted to be formed. Accordingly, excellent applicability can be secured.

Herein, any type of Vickers indenter, Knoop indenter, Berkovich type indenter, spherical indenter, and triangular pyramid type indenter, which are universally used, may be used as the indenter.

Any type of a device that can increase and decrease the load given to an indenter at an optional speed may be used as a load device without any special limitation. For example, a piezoelectric actuator and a stepping motor that is capable of increasing and decreasing the load by means of an electromagnetic force of an electromagnetic coil may be used.

A dynamic strain load converter utilizing a strain gauge, a chemical balance, a load-cell and electromagnetic type electronic balance, or a differential transformer, etc., may be used as the load sensor. Among these, an electronic even balance disposed at the lower part of a stage on which a test sample is placed may be preferably used, because the electronic even balance has remarkably high sensitivity and is able to detect a micro load, and highly accurate measurement can be brought about.

Further, the load applied to a test sample is not detected with the load sensor disposed at the lower part of the stage on which the test sample is placed, but a load sensor is attached to the load device, wherein the load applied to the test sample can be detected.

As a displacement meter, such a meter as utilizes electrostatic capacity, electromagnetic induction, magnetic field change, etc., utilizes optical interference, or utilizes a strain gauge, or utilizes a photonic sensor (Brand name: Photonics Inc., U.S.) may be used.

It is preferable that the calculating means has a feature of judging, by comparing the unloading data with the load data, whether or not the load fluctuation amount when unloading at the maximum depth $δ_0$ is within the first permissible range and calculating the hardness based on the judgment result in addition to a feature of judging whether or not the load or the load fluctuation amount is within the second permissible range and calculating the hardness based on the judgment result. Since the calculating means is able to calculate the hardness of a test sample in which deflection is unlikely to occur such as in metals, the applicability thereof is excellent.

Since the first permissible range and the second permissible range have already been described in regard to the first aspect of the invention, the description thereof is omitted.

The present invention is a micro-hardness meter discussed above, wherein a depth δ detected by the displacement meter is measured by an electrostatic capacity type sensor disposed between the underside of an extension portion extending sideways of an indenter support having an indenter placed at the tip end thereof and the surface of the test sample, and the load sensor is composed of an electronic even balance disposed at the lower part of the stage having the test sample placed thereon.

With the construction, the following actions can be brought about in addition to the actions discussed above.

Since the load sensor is composed of an electronic even balance, the balance has remarkably high sensitivity and is able to detect a change in micro load. Further, since the depth δ at which an indenter is pushed in a test sample is measured by an electrostatic capacity type sensor, it is possible to detect a minute change in depth. Therefore, the load data and the unloading data showing the relationship of the load L and depth 8 can be accurately measured, wherein highly accurate measurement of hardness of the test sample can be brought about.

As described above, with the micro-hardness measurement method and micro-hardness meter according to the present invention, the following advantageous effects can be brought about.

According to the present invention, it is possible to provide a micro-hardness measurement method which, since the load data when loading and the unloading data when unloading are extracted and the virtual depth $\delta_v$ is calculated based on these data, does not require any cumbersome operation that carries out correction by measuring the depth of the indentation and the length of the diagonal line thereof a plurality of times and calculating the correction value, and which may calculate the hardness with simple operations and is excellent in operability.

It is possible to provide a micro-hardness measurement method that is excellent in versatility and is able to calculate the hardness of either a test sample such as metals in which deflection is unlikely to occur or a test sample in which deflection is likely to occur such as a test sample in which a hard surface layer is formed on the surface of a substrate.

It is possible to provide a micro-hardness measurement method that almost accurately obtains the inclination of a tangent line at depth $\delta_1$ of the load curve and the inclination of a tangent line at the maximum depth $\delta_0$ of the unloading curve since the load curve and the unloading curve in the vicinity of the maximum depth $\delta_0$ are comparatively simple, wherein an error is unlikely to occur, and is able to calculate the hardness at high accuracy without being influenced by the profile of an indenter.

It is possible to provide a micro-hardness measurement method that is excellent in applicability and is able to calculate the hardness of a test sample having such a hard surface layer, on which only a micro load is permitted to be loaded, and only a micro indentation whose diagonal line length is 10 micrometers or less is permitted to be formed since it is not necessary to measure the actual depth of an indentation and the actual length of the diagonal line of an indentation.

According to the present invention, in addition to the effects discussed above, it is possible to provide a micro-hardness measurement method that is able to simplify setting of the first permissible range, has high detection sensitivity, wherein an error is unlikely to occur, and is able to measure the hardness at high accuracy since it is judged, in the first judging step, whether or not a conversion value $n_0/m_0$ of the ratio of the inclinations $n_0$ and $m_0$ of tangent lines exceeds the upper limit of the first permissible range.

According to the present invention, in addition to the effects discussed above, it is possible to provide a micro-hardness measurement method that is able to simplify setting of the second permissible range, has high detection sensitivity, wherein an error is unlikely to occur, and is able to measure the hardness at high accuracy since it is judged, in the second judging step, whether or not a conversion value $n_1/m_1$ of the ratio of the inclinations $n_1$ and $m_1$ of tangent lines exceeds the upper limit of the second permissible range.

According to the present invention, it is possible to provide a micro-hardness meter that is able to calculate the hardness in a short time and is excellent in operability since no cumbersome operation is required, which carries out correction by measuring the depth of the indentation and the length of the diagonal line thereof a plurality of times and calculating the correction value.

It is possible to provide a micro-hardness meter that is able to calculate the hardness at high accuracy without being influenced by the profile of an indenter, wherein an error is unlikely to occur.

It is possible to provide a micro-hardness meter having excellent applicability that is able to calculate the hardness of a test sample having such a hard surface layer, on which only a micro load is permitted to be loaded, and only a micro indentation whose diagonal line length is 10 micrometers or less is permitted to be formed since it is not necessary to measure the actual depth of an indentation and the actual length of the diagonal line of the indentation.

According to the present invention, in addition to the effects discussed above, it is possible to provide a micro-hardness meter that is able to accurately measure the load data and unloading data showing the relationship between the load L and depth $\delta$ since a minute change in load and a minute change in depth can be detected, and is able to measure the hardness of a test sample at high accuracy.

DESCRIPTION OF THE INVENTION

Hereinafter, a description is given of the best mode for carrying out the invention with reference to the drawings.

Embodiment 1

Figure 1:
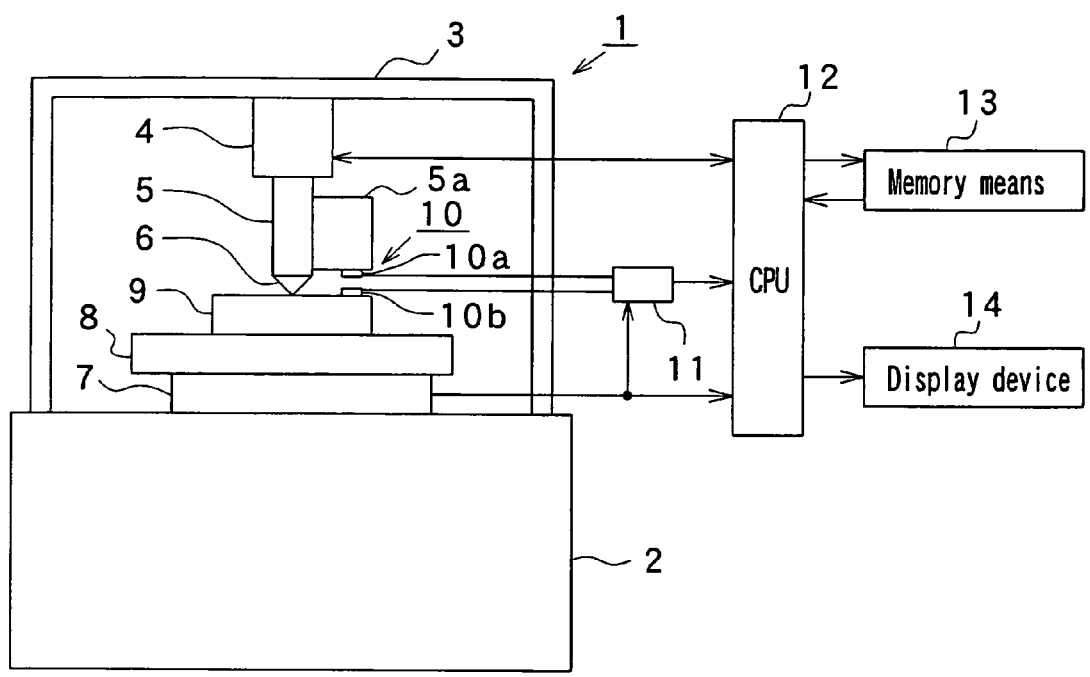
FIG. 1 is a block diagram showing a micro-hardness meter according to one embodiment consistent with the present invention.
Figure 2:
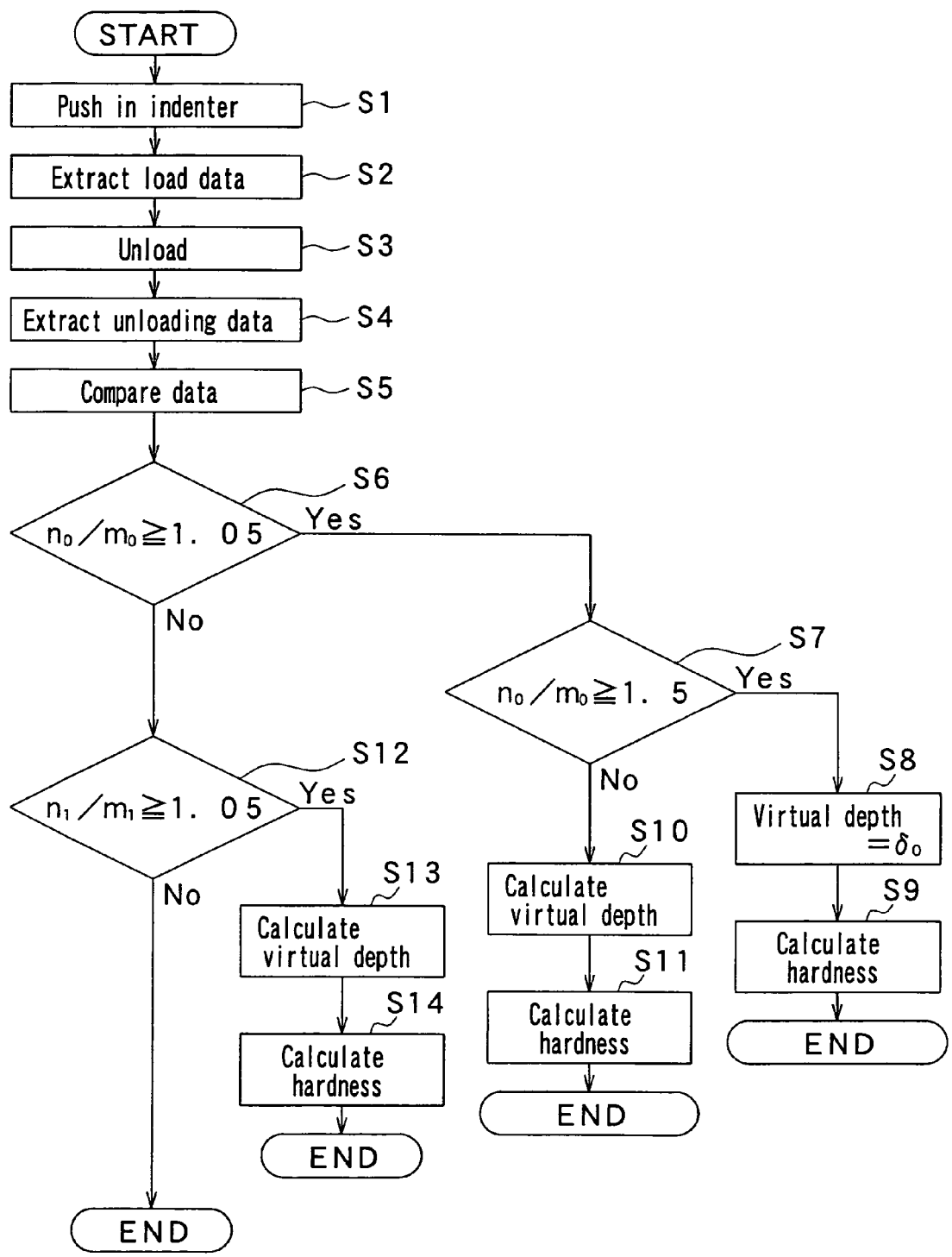
FIG. 2 is a flowchart showing actions in the micro-hardness meter.
Figure 3:
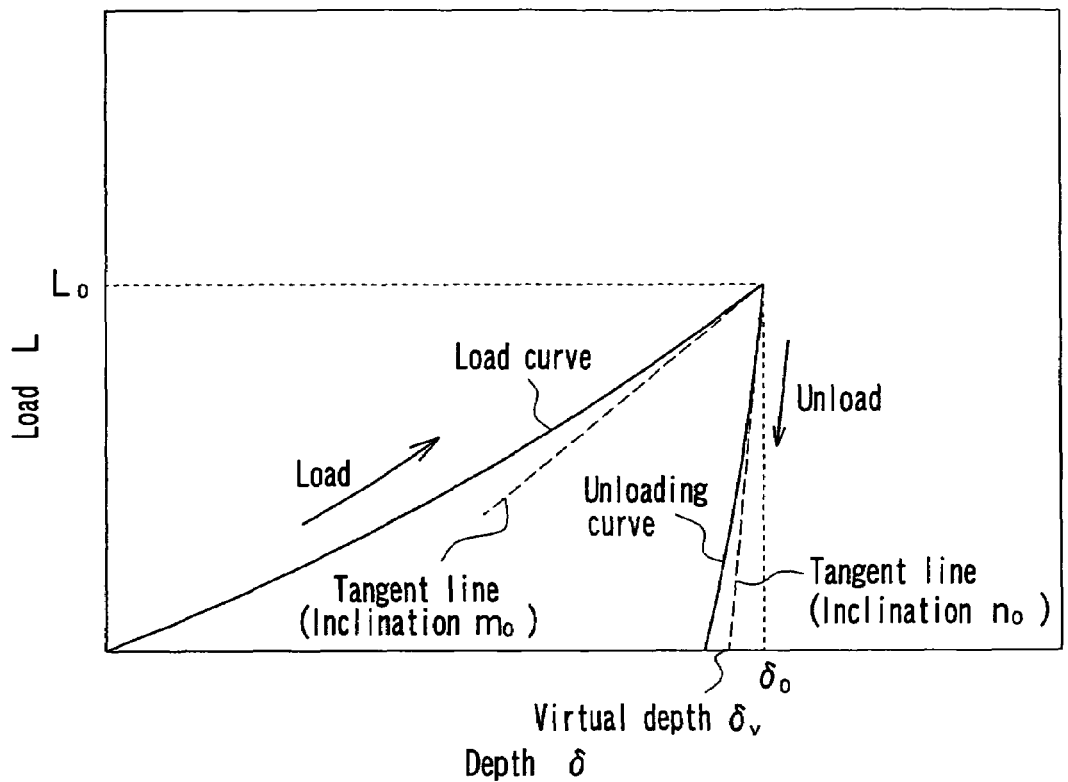
FIG. 3 is a view showing the calculation principle of virtual depth $\delta_v$.
Figure 4:
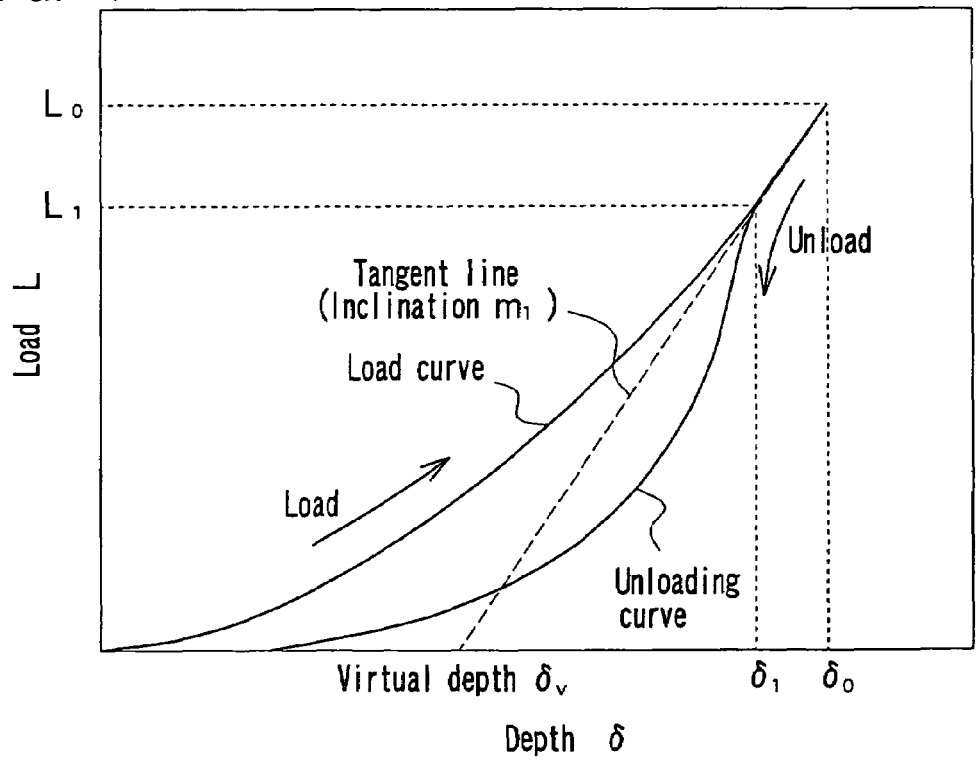
FIG. 4 is a view showing the calculation principle of virtual depth $\delta_v$.

FIG. 1 is a block diagram depicting a micro-hardness meter according to one embodiment of the invention, FIG. 2 is a flowchart depicting actions of the micro-hardness meter, and FIG. 3 and FIG. 4 are views depicting the calculation principle of virtual depth $\delta_v$.

In FIG. 1, reference numeral 1 denotes a micro-hardness meter according to one embodiment of the invention, 2 denotes a base portion of the micro-hardness meter 1, 3 denotes a frame body erected on the base portion 2, and 4 denotes a load device composed of a piezoelectric actuator and a stepping motor, etc., which is able to increase and decrease the load given to an indenter 6 vertically suspended from the frame body 3 and described later at an optional speed. Reference numeral 5 denotes an indenter support vertically suspended from the load device 4, 5a denotes an extension portion extending sideways of the indenter support 5 and vertically moving along with the indenter support 5, 6 denotes a Vickers or Knoop type indenter disposed at the tip end of the indenter support 5, 7 denotes a load sensor disposed on the base portion 2 and composed of an electronic balance, and 8 denotes a stage disposed on the upper part of the load sensor 7. Reference numeral 9 denotes a test sample disposed on the stage 8, 10 denotes a displacement sensor disposed on the surface of the test sample 9 separated by 10 millimeters or so from the tip end of the indenter 6 on the underside of the extension portion 5a. The displacement sensor 10 according to one embodiment is an electrostatic capacity type sensor that is provided with a pair of electrode plates 10a and 10b on the upper and lower faces thereof, is placed between the underside of the extension portion 5a and the surface of the test sample 9, and detects the relative distance between the surface of the test sample 9 and the underside of the extension portion 5a by utilizing an electrostatic capacity changing in line with a change in interval between the electrode plates 10a and 10b. Since the displacement sensor 10 is disposed on the surface of the test sample 9 which is separated by 10 millimeters or so from the tip end of the indenter 6, the displacement sensor is not influenced by displacement on the surface of the test sample 9 in the extreme vicinity of the indenter 6, which is produced by the indenter 6 being pushed in the test sample 9, wherein the interval between the electrode plates 10a and 10b may be used as a reference of the relative distance from the surface of the test sample 9 to the underside of the extension portion 5a.

Reference numeral 11 denotes a displacement meter for converting signals from the displacement sensor 10 to data of the relative distance from the surface of the test sample 9 to the underside of the extension portion 5a. The displacement meter 11 according to one embodiment judges, when the load sensor 7 detects a load of the indenter 6, that the indenter 6 has been brought into contact with the surface of the test sample 9, calculates the displacement amount of the displacement sensor 10 from the distance based on the data of distance from the displacement meter 11 at that time, and regards the displacement amount as the depth $\delta$ by which the indenter 6 is pushed in from the surface of the test sample 9. In addition, the depth $\delta$ includes both the depth of a depression formed on the surface of the test sample 9 by pushing the indenter 6 into the test sample 9 and the deflection amount of the test sample 9.

Reference numeral 12 denotes a central processing unit (CPU) acting as means for carrying out calculations based on the load data from the load sensor 7 and the data of depth $\delta$ from the displacement meter 11. Reference numeral 13 denotes memory means such as RAM for storing load data from the load sensor 7 and data of depth $\delta$ from the displacement meter 11 at each time elapsed after the load sensor 7 detects a load of the indenter 6. Reference numeral 14 denotes a display device such as an XY plotter, a display, etc., for outputting load-displacement curves, etc., based on the load data from the load sensor 7 and data of depth $\delta$ from the displacement meter 11.

With reference to FIG. 2, a description is given of the operations of the micro-hardness meter according to one embodiment of the invention, which has been constructed as described above.

When the power source of the micro-hardness meter 1 is turned on, after the load device 4 causes the indenter support 5 and the extension portion 5a to descend, and causes the indenter 6 to be brought into contact with the test sample 9, the indenter 6 is lowered at a fixed speed in the loading step and the indenter 6 is continuously pushed in the test sample 9 until the load reaches the maximum load $L_0$ (that is, the established test force) (S1). The load sensor 7 transmits data of the load applied by the indenter 6 onto the test sample 9 to the CPU 12. The displacement meter 11 converts the signals transmitted by the displacement sensor 10 to data of depth $\delta$ at which the indenter 6 is pushed in the test sample 9, and transmits the same to the CPU 12. The CPU 12 extracts load data showing the relationship between load and displacement when being loaded, based on the data of depth $\delta$ transmitted from the displacement meter 11 and the data of load from the load sensor 7, and causes the same to be stored in the memory means 13 (S2). Also, the CPU 12 extracts data showing the relationship between the time T and depth $\delta$ by which the load is applied to the indenter 6 and data showing the relationship between the time T and load when the load is applied to the indenter 6, and further extracts load data showing the relationship between the load and the displacement by synthesizing these two types of data.

As the load reaches the maximum load $L_0$, the load device 4 maintains the maximum load $L_0$ for a fixed period of time. After that, the load device 4 unloads the load in the unloading step and raises the indenter 6 at a fixed speed (S3). Taking the rate of elastic restoration of the test sample 9 into consideration, the load device 4 elevates the indenter 6 at a speed of 0.1 through 1 micrometer per second so that the histories of the unloading data and the load data can be distinguished from each other. The load sensor 7 transmits data of the load applied by the test sample 9 onto the indenter 6 due to elastic restoration of the test sample 9 to the CPU 12. The displacement sensor 10 transmits data of displacement of the indenter 6 to the displacement meter 11, and the displacement meter 11 converts the data transmitted by the displacement sensor 10 to data of depth $\delta$ to which the indenter 6 is pushed in from the surface of the test sample 9, and transmits the same to the CPU 12. The CPU 12 extracts unloading data showing the relationship between load and displacement when being unloaded, based on the data transmitted from the load sensor 7 and displacement meter 11, and causes the same to be stored in the memory means 13 (S4). Also, the CPU 12 extracts data showing the relationship between time T and depth $\delta$ when the load is unloaded and data showing the relationship between time T and load when the load is unloaded, and may extract load data showing the relationship between load and displacement by synthesizing these two types of data.

In the first judging step, the CPU 12 compares the load data and the unloading data with each other, which are stored in the memory means 13 (Step 5), and judges whether or not the load fluctuation amount from the maximum depth $\delta_0$ when unloading is within the first permissible range. The load fluctuation amount from the maximum depth $\delta_0$ when unloading may be expressed by an inclination of a tangent line at the maximum depth $\delta_0$ of the unloading curve obtained from the unloading data. The inclination may be obtained by differentiating the unloading curve. In addition, it may be obtained from the unloading data by means of a difference calculus. Further, in the present embodiment, the first permissible range is established by using, as an index, a conversion value $n_0/m_0$ of the ratio of the inclination $n_0$ of a tangent line at the maximum depth $\delta_0$ of the unloading curve to the inclination $m_0$ of a tangent line at the maximum depth $\delta_0$ of the load curve, and $n_0/m_0=1.05$ is defined as an upper limit.

In the first judging step, it is judged whether or not $n_0/m_0 \geq 1.05$ is established (S6). Where $n_0/m_0 \geq 1.05$, next it is judged whether or not $n_0/m_0 \geq 1.5$ (S7). $n_0/m_0=1.5$ is a threshold value for determining whether or not the maximum depth $\delta_0$ is regarded as a depth (virtual depth $\delta_v$) by which the surface area of an indentation (permanent depression) formed on the test sample 9 may be calculated, and it may be appropriately established. Where $n_0/m_0 \geq 1.5$ is established in S7, it means that the unloading curve is greatly deviated from the load curve, wherein since plastic deformation is dominative in the indentation, the maximum depth $\delta_0$ shown in FIG. 3 is regarded as the depth (virtual depth $\delta_v$) by which the surface area of the indentation (permanent depression) formed on the test sample 9 (S8) can be calculated. Next, in the hardness calculating step, the CPU 12 calculates the hardness by calculating the surface area of a permanent depression based on the virtual depth $\delta_v$ and by calculating (Maximum load $L_0$)/(Surface area of permanent depression) (S9).

Where $n_0/m_0<1.5$ is established (that is, $1.05 \leq n_0/m_0<1.5$) in S7, it means that the unloading curve from the maximum depth $\delta_0$ is slightly deviated from the load curve, wherein if the maximum depth $\delta_0$ is regarded as the virtual depth $\delta_v$, the error becomes large. Therefore, the virtual depth $\delta_v$ is calculated by the interpolation method (S10). In the present embodiment, the virtual depth $\delta_v$ is calculated by the interpolation expression (4).

$$\delta_v = \delta_0 - (L_0/m_0) \times (1.5 - n_0/m_0)/(1.5 - 1.05) \quad (4)$$

Next, in the hardness calculating step, the CPU 12 calculates the surface area of the permanent depression based on the virtual depth $\delta_v$ and calculates the hardness by calculating (Maximum load $L_0$)/(Surface area of permanent depression) (S11).

Where the CPU 12 judges, in S6, that the load fluctuation amount when unloading from the maximum depth $\delta_0$ is within the first permissible range, that is, $n_0/m_0<1.05$, the CPU 12 compares the load data of a depth $\delta_1$ ($\delta_1<\delta_0$) in a shallower area than the maximum depth $\delta_0$ stored in the memory means 13 with the unloading data in the second judging step, and judges whether or not the fluctuation amount of the load $L_1$ in the vicinity of the depth $\delta_1$ when unloading is within the second permissible range (S12). The load fluctuation amount when unloading may be expressed by an inclination of a tangent line at the depth $\delta_1$ of the unloading curve obtained from the unloading data, and the inclination may be obtained by differentiating the unloading curve, and may be obtained from the unloading data by means of a difference calculus. In addition, in the present embodiment, the second permissible range is established by using, as an index, the conversion value $n_1/m_1$ of the ratio of the inclination $n_1$ of a tangent line at the maximum depth $\delta_1$ of the unloading curve to the inclination $m_1$ of a tangent line at the depth $\delta_1$ of the load curve, and $n_1/m_1=1.05$ is defined as an upper limit.

In the second judging step, it is judged whether or not $n_1/m_1 \geq 1.05$ is established, and if $n_1/m_1 \geq 1.05$ is secured, it is judged that the load fluctuation amount is not within the second permissible range. In the virtual depth calculating step, the virtual depth $\delta_v$ is calculated based on the tangent line (shown by the dotted chain line in FIG. 4) at the depth $\delta_1$ of the load curve obtained from the load data (S13). The virtual depth $\delta_v$ is located at a point of intersection between the $\delta$ axis shown in FIG. 4 and the equation of the tangent line, and shows the depth at which the surface area of an indentation (permanent depression) formed in the test sample 9 can be calculated. Next, in the hardness calculating step, the CPU 12 calculates the surface area of a permanent depression based on the virtual depth $\delta_v$ and calculates the hardness by calculating (Maximum load $L_0$)/(Surface area of permanent depression) (S14).

When the CPU 12, in S12, calculates $n_1/m_1$ at all the depths $\delta_1$ ($0<\delta_1<\delta_0$) when being unloaded, and resultantly judges that $n_1/m_1<1.05$ is secured at the all the depths $\delta_1$, it means that only elastic deformation occurs in the test sample 9 due to a load of the indenter 6 and no permanent depression is formed, wherein since the hardness may not be calculated, the hardness measurement is terminated.

Also, the CPU 12 can display the load data, unloading data, load curve, and unloading curve by using a display device 14.

Also, in the present embodiment, the upper limit of the first permissible range is set to $n_0/m_0=1.05$ in the first judging step, and the upper limit of the second permissible range is set to $n_1/m_1=1.05$. The reason is that, as the upper limit becomes smaller than 1.05, it is likely to be judged that a slight difference between the load data and the unloading data brings about a deviation from the permissible range, the tendency of the virtual depth $\delta_v$ being estimated to be deeper than the depth of an indentation is intensified, and the tendency of the hardness being underestimated becomes remarkable. In addition, if the upper limit becomes larger than 1.05, the detection sensitivity is lowered.

In the present embodiment, the setting is made so that it is judged whether or not $n_0/m_0 \geq 1.5$ is established when $n_0/m_0 \geq 1.05$ is established in the first judging step. The reason is that, as the upper limit becomes smaller than 1.5, the tendency of the virtual depth $\delta_v$ being estimated to be deeper than the depth of an indentation is intensified, and the tendency of the hardness being underestimated becomes remarkable, and it is found that there is no great difference between the depth $\delta$ obtained by the interpolation method and the maximum depth $\delta_0$ even if the upper limit becomes larger than 1.5.

Since the micro-hardness meter according to one embodiment of the present invention is constructed as described above, the following actions can be obtained.

Where the indenter 6 is pushed in the test sample 9, in which deflection due to elastic deformation is likely to occur, such as a test sample in which a hard surface layer is formed on the surface of a soft substrate, and the load is unloaded after the maximum load $L_0$ is applied, the load L which is the same as that when loading is applied from the test sample 9 to the indenter 6 by elastic restoration of the test sample 9 at the beginning of unloading if the indenter 6 does not completely destroy the surface layer of the test sample 9. Therefore, the unloading data at the beginning of unloading is almost coincident with the load data. Since the restoration force of the test sample 9 is made small as the unloading advances and the deflection of the test sample 9 is made small, the load L applied from the test sample 9 onto the indenter 6 is made smaller than the load L applied by the indenter 6 onto the test sample 9 when being loaded, and is deviated from the load data. Utilizing the characteristics, the load data are stored in the memory means 13 and are compared with the unloading data by using the CPU 12, wherein it is judged whether or not the load fluctuation amount when unloading at a depth $\delta_1$ is within the second permissible range. When it is judged that the load fluctuation amount is not within the second permissible range, a tangent line (inclination $m_1$) of the load curve obtained from the load data is obtained, the depth is calculated in regard to the load $L=0$ (where completely unloaded) of the tangent line, and the calculated depth is regarded as the depth (virtual depth $\delta_v$) calculated from the surface area of an indentation (permanent depression), wherein the hardness can be calculated based on the virtual depth $\delta_v$ and the maximum load $L_0$.

The CPU 12 judges whether or not the conversion value $n_0/m_0$ of the ratio of the inclination $n_0$ of a tangent line at the maximum depth $\delta_0$ of the unloading curve to the inclination $m_0$ of a tangent line at the maximum depth $\delta_0$ of the load curve is within the first permissible range, and when $n_0/m_0 \geq 1.5$ is established, the maximum depth $\delta_0$ is regarded as the depth (virtual depth $\delta_v$) by which the surface area of an indentation (permanent depression) formed on the test sample 9 can be calculated, and when $1.05 \leq n_0/m_0<1.5$ is established, the virtual depth $\delta_v$ is calculated by the interpolation method. Accordingly, it is possible to measure the hardness of a test sample in which deflection is unlikely to occur due to elastic deformation such as in metals, wherein applicability is excellent.

Since the load data by which the indenter 6 is applied load and is pushed in the test sample 9 and the unloading data when unloading from the indenter 6 are extracted, and the virtual depth $\delta_v$ is calculated based on these data, no cumbersome operation is required, which carries out correction by measuring the depth of the indentation and the length of the diagonal line thereof a plurality of times and calculating the correction value. Therefore, the hardness can be calculated with simple operations and the operability thereof is excellent.

Since the load curve is comparatively simple, the CPU 12 is able to almost accurately obtain the inclination of a tangent line at the depth $\delta_1$ of the load curve, wherein an error is unlikely to occur, and the hardness can be calculated at high accuracy without being influenced by the profile of the indenter 6.

Since it is not necessary to measure the actual depth of an indentation and actual length of a diagonal line of the indentation, it is possible to further calculate the hardness of a test sample having such a hard surface layer, on which only a micro load is permitted to be loaded, and only a micro indentation whose diagonal line length is 10 micrometers or less is permitted to be formed. Therefore, applicability is excellent.

Since the load sensor 7 composed of an electronic balance can be used, the load sensor 7 has remarkably high sensitivity and it is possible to detect a slight change in the load. Furthermore, since the depth $\delta$ at which the indenter 6 is pushed in the test sample 9 can be measured by the displacement sensor 10 of the electrostatic capacity type sensor, a slight change in depth can be detected. Therefore, it is possible to accurately measure the load data and the unloading data, which show the relationship between the load L and the depth $\delta$, wherein the hardness of a test sample can be measured at high accuracy.

Also, with the micro-hardness measurement method according to Embodiment 1 as described above, the following actions can be brought about.

Since the load data when being loaded and the unloading data when being unloaded are extracted, and the virtual depth $\delta_v$ is calculated based on these data, no cumbersome operation is required, which carries out correction by measuring the depth of the indentation and the length of the diagonal line thereof a plurality of times and calculating the correction value. Therefore, the hardness can be calculated with simple operations and the operability thereof is excellent.

It is possible to calculate the hardness of either a test sample in which deflection is unlikely to occur such as in metals or a test sample in which deflection is likely to occur such as in a test sample in which a hard surface layer is formed on the surface of a substrate. Therefore, the versatility is excellent.

Since the load curve and the unloading curve in the vicinity of the maximum depth $\delta_0$ are comparatively simple, the inclination $m_1$ of a tangent line at depth $\delta_1$ of the load curve and the inclination $n_0$ of a tangent line at the maximum depth $\delta_0$ of the unloading curve can be almost accurately obtained, wherein an error is unlikely to occur, and is able to calculate the hardness at high accuracy without being influenced by the profile of an indenter.

Since it is not necessary to measure the actual depth of an indentation and actual length of a diagonal line of the indentation, it is possible to further calculate the hardness of a test sample having such a hard surface layer, on which only a micro load is permitted to be loaded, and only a micro indentation whose diagonal line length is 10 micrometers or less is permitted to be formed. Therefore, applicability is excellent.

In addition, although, in the present embodiment, the displacement sensor 10 is an electrostatic capacity type sensor that utilizes changes in the electrostatic capacity, a sensor having high measurement accuracy may be selected from sensors that utilize changes in electromagnetic induction, magnetic field, etc., utilize optical interference, utilize a strain gauge, and utilize a photonic sensor (for example, by Photonics Inc., US), may be appropriately used.

Also, although an electronic even balance disposed on the underside of the stage 8 is used as the load sensor 7, a dynamic strain type load converter using a strain gauge, etc., a chemical balance, a load-cell type and an electromagnetic-type balance, etc., may be used. Further, it may be constructed that the load can be detected at the load device 4 side.

Further, in the present embodiment, since the virtual depth $\delta_v$ are obtained in the cases of $1.05 \leq n_0/m_0 < 1.5$, $n_0/m_0 \geq 1.05$, and $n_1/m_1 \geq 1.05$, respectively, 1.05 or 1.5 are established as the threshold values of $n_0/m_0$ and $n_1/m_1$. The threshold values may be set in an almost fixed range, not depending on the material of the test sample. In addition, a preparatory experiment is carried out while varying the speed of the indenter when unloading, and the threshold values may be appropriately established in response to the result.

EXAMPLE

Hereinafter, a detailed description is given of the present invention by referring to an example. The present invention is not limited to the example.

Example 1

The hardness of a test sample in which a hard glass layer 5 through 10 micrometers thick is formed on the surface of a polycarbonate substrate (10 millimeters thick) was measured by using the micro-hardness meter described in one embodiment.

The test sample was placed on the stage and a Vickers indenter was pushed in from the surface of the test sample at a rate of 0.2 micrometers per second. After being loaded to the maximum load (the established test force) $L_0$=109 mN, the maximum load $L_0$ was retained for 15 seconds, and next the load of the indenter was unloaded. Finally, the indenter was pulled up from the test sample at the rate of 0.2 micrometers per second same as that when loading.

Figure 5:
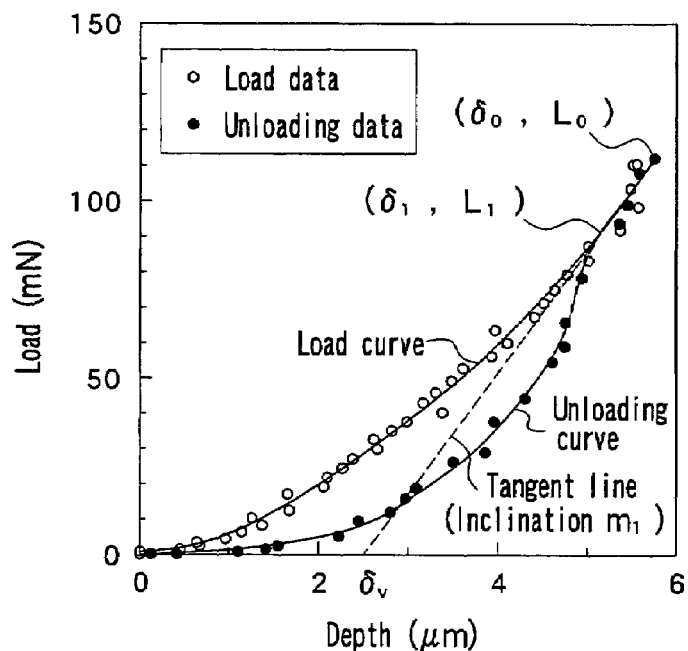
FIG. 5 is a view showing the load data, load curve, unloading data, unloading curve and virtual depth $\delta_v$ in Example 1.
Figure 6A:
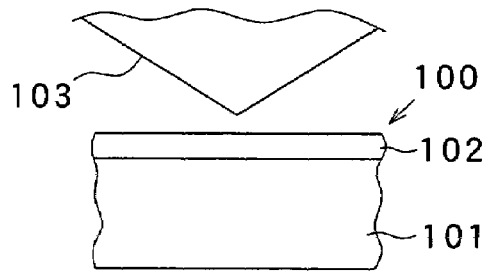
FIG. 6 is a schematic view showing the situations where an indenter is pushed in a test sample in which a hard surface layer is formed on the surface of a soft substrate.
Figure 6B:
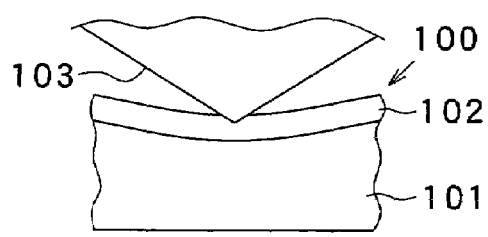
Figure 6C:
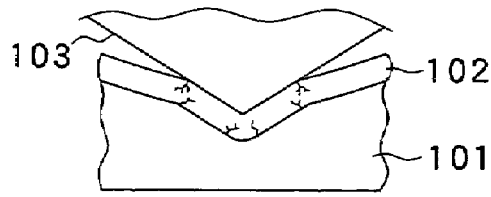
Figure 6D:
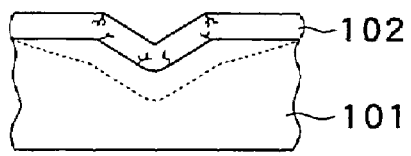

FIG. 5 is a view showing the load data, load curve, unloading data, unloading curve and virtual depth $\delta_v$ in Example 1. The abscissa thereof shows the depth and the ordinate thereof shows the load. White circles show actually measured load data while black circles show actually measured unloading data. Solid lines show a load curve and a unloading curve while a broken line shows tangent lines (inclination $m_1$) of the load curve at depths $\delta_1$ deviated from the second permissible range.

In the case of Example 1, since the virtual depth $\delta_v$ could be obtained to 2.5 micrometers by calculating the expression of tangent lines (Inclination $m_1$), it was possible that the Vickers hardness Hv=660 Mpa of the test sample could be calculated by substituting $\delta$ and $L_0$ in the definition expression $Hv=1.85437 \times \{L_0/(\delta/0.1428)^2\}$ of the Vickers hardness Hv.

In addition, in the case of the present example, it was found that the Vickers hardness thus calculated depends on the size of the maximum load (test force) applied to the test sample. This is because the virtual depth $\delta_v$ and the surface area of the permanent depression change, depending on the size of the maximum load. In detail, there is such a tendency as described below, that is, the lower the maximum load $L_0$ applied to the test sample becomes than 109 mN, the more the influence of the hard glass layer on the surface of the test sample becomes, wherein since the virtual depth $\delta_v$ is shallow, and the surface area of the permanent depression is decreased, the Vickers hardness is increased. To the contrary, the higher the maximum load $L_0$ applied to the test sample becomes than 109 mN, the more the influence of polycarbonate being the substrate of the test sample becomes, wherein since the virtual depth $\delta_v$ is deep, and the surface area of the permanent depression is increased, the Vickers hardness is made lower.

As described above, according to the present example, no cumbersome operation is required, which carries out correction by measuring the depth of the indentation and the length of the diagonal line thereof a plurality of times and calculating the correction value. Therefore, the hardness can be calculated with simple operations and the operability thereof is excellent. In addition, it is possible to calculate the hardness of a test sample having such a hard surface layer, on which only a micro load is permitted to be loaded, and only a micro indentation is permitted to be formed, whereby excellent applicability was confirmed.

Thus, the present invention relates to a micro-hardness measurement method for measuring the hardness of a test sample by forming an indentation or impression by pushing an indenter into a test sample, and a micro-hardness meter therefore, and in particular, to a micro-hardness measurement method and a micro-hardness meter, which are best suitable for measuring the hardness of a test sample in which a hard surface layer is formed on the surface of a soft substrate. A micro-hardness measurement method having excellent applicability can be brought about, wherein, since no cumbersome operation is required, which carries out correction by measuring the depth of the indentation and the length of the diagonal line thereof a plurality of times and calculating the correction value, the hardness can be calculated with simple operations, and excellent operability can be secured, further, an error is unlikely to occur and the hardness can be calculated at high accuracy without being influenced by the profile of an indenter, and it is possible to calculate the hardness of a test sample having such a hard surface layer, on which only a micro load is permitted to be loaded, and only a micro indentation whose diagonal line length is 10 micrometers or less is permitted to be formed. Still further, a micro-hardness meter having excellent operability, which is capable of automatically calculating the hardness in a short time, calculating the same at high accuracy without being influenced by the profile of an indenter, wherein an error is unlikely to occur, and further calculating the hardness of a test sample having such a hard surface layer, on which only a micro load is permitted to be loaded, and only a micro indentation whose diagonal line length is 10 micrometers or less is permitted to be formed, therefore being excellent in applicability.

What is claimed is:

1. A micro-hardness measurement method for calculating the hardness by pushing an indenter in a test sample and forming an indentation, comprising:

extracting load data showing the a relationship between load L applied to the indenter and a depth $\delta$, to which the indenter is pushed in from a surface of the test sample, to a maximum load $L_0$, which is a load at a maximum depth $\delta_0$;

extracting unloading data showing a relationship between the load L applied to the indenter after the load is unloaded and the depth $\delta$;

judging, by comparing the unloading data with the load data, whether or not a load fluctuation amount from the maximum depth $\delta_0$ when unloading the load is within a first permissible range;

judging, when it is judged that the load fluctuation amount is within the first permissible range, whether or not the load at the depth $\delta_1$ ($\delta_1<\delta_0$) when unloading the load or the load fluctuation amount in a vicinity of the depth $\delta_1$ is within a second permissible range;

calculating a virtual depth $\delta_v$ based on an inclination of a tangent line at the maximum depth $\delta_0$ of an unloading curve obtained from the unloading data (a) when it is judged, one of that the load fluctuation amount is not within the first permissible range, or regarding the maximum depth $\delta_0$ as a virtual depth $\delta_v$, or of calculating a virtual depth $\delta_v$ based on an inclination of a tangent line at the depth $\delta_1$ of a load curve obtained from the load data, (b) when it is judged that the load or the load fluctuation amount is not within the second permissible range; and calculating the hardness based on the virtual depth $\delta_v$ and the maximum load $L_0$.

2. The micro-hardness measurement method according to claim 1, wherein the upper limit of the first permissible range is defined by a conversion value $n_0/m_0$ of a ratio of an inclination $n_0$ of a tangent line at the maximum depth $\delta_0$ of the unloading curve to an inclination $m_0$ of a tangent line at the maximum depth $\delta_0$ of the load curve.

3. The micro-hardness measurement method according to claim 1, wherein an upper limit of the second permissible range is defined by a conversion value $n_1/m_1$ of a ratio of the an inclination $n_1$ of a tangent line at the depth of the unloading curve $\delta_1$ ($\delta_1<\delta_0$) of the unloading curve to an inclination $m_1$ of a tangent line at the depth $\delta_1$ of the load curve.

4. A micro-hardness meter comprising:

(a) a load device for forming an indentation on a test sample by applying a load to an indenter:

(b) a load sensor for detecting a load L at which the indenter applies to the test sample when loading, and a load L at which the test sample applies to the indenter when unloading;

(c) a displacement meter for detecting a depth $\delta$ to which the indenter is pushed in from a surface of the test sample;

(d) memory means for storing, based on information from the load sensor and the displacement meter, load data showing a relationship between the load L and the depth $\delta$ when loading, unloading data showing a relationship between the load L and the depth $\delta$ when unloading, and a maximum depth $\delta_0$ and a maximum load $L_0$ (load at a maximum depth $\delta_0$); and (e) calculating means for comparing the unloading data with the load data and judging whether or not the load at the depth $\delta_1$ ($\delta_1<\delta_0$) when unloading or a load fluctuation amount in a vicinity of the depth $\delta_1$ is within a second permissible range, calculating a virtual depth $\delta_v$ based on an inclination of a tangent line at the depth $\delta_1$ of the load curve, which is obtained from the load data, when it is judged that the load or the load fluctuation amount is not within the second permissible range, and calculating the hardness based on the virtual depth $\delta_v$ and the maximum load $L_0$.

5. The micro-hardness meter according to claim 4, wherein a depth $\delta$ detected by the displacement meter is measured by an electrostatic capacity type sensor disposed between an underside of an extension portion extending sideways of an indenter support having an indenter placed at a tip end thereof and the surface of the test sample, and the load sensor is composed of an electronic even balance disposed at a lower part of a stage having the test sample placed thereon.

* * * * *